United States Patent [19]

Cardina et al.

[11] Patent Number: 4,643,756

[45] Date of Patent: Feb. 17, 1987

[54] BIOHERBICIDE FOR FLORIDA BEGGARWEED

[75] Inventors: John Cardina; Robert H. Littrell, both of Tifton, Ga.; Larry J. Stowell, San Diego, Calif.

[73] Assignees: Mycogen Corporation, San Diego, Calif.; Univ. of Georgia Research Foundation, Inc., Athens, Ga.; The United States of America as represented by the Secretary of Agriculture, Washington, D.C.

[21] Appl. No.: 715,229

[22] Filed: Mar. 22, 1985

[51] Int. Cl.⁴ .............................. A01N 63/00
[52] U.S. Cl. ........................ 71/79; 435/911
[58] Field of Search ............ 71/79; 435/911; 47/DIG. 11

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,162,912 | 7/1979 | Charudatan | 71/79 |
| 4,263,036 | 4/1981 | Charudattan | 71/79 |
| 4,390,360 | 6/1983 | Walker | 71/79 |
| 4,419,120 | 12/1983 | Walker | 71/79 |

OTHER PUBLICATIONS

Staples et al, "Appressorium Formation, etc.," (1976), Archives of Microbiology, vol. 109, pp. 75–84 (1976).
Almeida et al, "Curative and Preventative, etc.," (1981) CA 96: 29819s (1982).
Malhotra et al, "Utilization of Oligosaccharides, etc.," Pantnagar J. Res., (1977) 2(2), pp. 119–122.

*Primary Examiner*—Glennon H. Hollrah
*Assistant Examiner*—Robert Lelkes
*Attorney, Agent, or Firm*—Roman Saliwanchik; David R. Saliwanchik

[57] ABSTRACT

The subject invention concerns a novel bioherbicide and its use to control a major weed found in many fields in the Southeastern United States where peanuts and soybeans are grown. Specifically, *Colletotrichum truncatum* (Schw.) Andrus & Moore, in an agricultural composition, can be used to effectively control Florida beggarweed without adversely affecting field crops, e.g., peanuts and soybeans. Further, *C. truncatum* (Schw.) Andrus & Moore in a mixture with *Alternaria cassiae* can be used to control Florida beggarweed and other undesired vegetation, such as sicklepod, showy crotalaria and coffee senna.

6 Claims, No Drawings

BIOHERBICIDE FOR FLORIDA BEGGARWEED

BACKGROUND OF THE INVENTION

Florida beggarweed (*Desmodium tortuosum* (SW.)DC) is a major weed problem in many fields in the Southeastern United States where peanuts and soybeans are grown. It is ranked as the most troublesome weed in peanuts in the three largest peanut producing states, and its spread is causing increasing concern to farmers throughout the Southeast. This weed occurs primarily in field crops, but is found also in fallowed areas and along roadsides and waste areas. Florida beggarweed is an annual herbaceous legume native to Florida and the Gulf States, extending to the subtropics and tropics of the Western Hemisphere. Although it is currently considered one of the most damaging weeds, particularly in leguminous crops, Florida beggarweed was a popular forage crop prior to 1950. As a forage crop, heavy seeding on land of moderate to high fertility was recommended so that when plants matured 70–80 days later, the crop could be expected to yield 4 to 6 tons of dry matter and return to the soil up to 5000 seeds per plant. As a result, Florida beggarweed, no longer considered an acceptable forage crop, plagues farmers throughout the Southeast on soils that are most suitable for peanuts and soybeans. The damage caused by Florida beggarweed is primarily a result of competition with the field crop for light, water, and nutrients. In addition, this weed, which may reach 10 feet at maturity, overtops the crop canopy and interferes with pesticidal spray programs. Particularly serious is the decreased coverage of biweekly foliar fungicide applications in peanuts caused by infestations of Florida beggarweed. In peanut production, where the crop must be inverted at the end of the season, Florida beggarweed interferes with the digging, turning and curing processes, and thereby causes further reductions in crop yield and quality.

Florida beggarweed harbors several pests of field crops. It is a common late-season food source for *Heliothis virescens* larvae, a pest of numerous crops. This weed is also a host of northern rootknot, lesion and sting nematodes that severely damage many crops. Recent evidence indicates that Florida beggarweed is a host of peanut mottle virus and peanut stripe virus.

Florida beggarweed is a leguminous weed that is not controlled by herbicide programs recommended for use in peanuts and soybeans. Development of chemical control for Florida beggarweed is complicated by its close botanical relationship to peanuts, soybeans, and other leguminous crops. This puts unusually stringent selectivity requirements on development of herbicides.

Chemical weed control programs are seriously inadequate for control of this weed. Florida beggarweed is resistant to many herbicides used in peanuts and soybeans. Frequently the weed germinates below the treated zone and avoids herbicide injury. Although many herbicides have been developed and tested in the last three decades, farmers still rely heavily on dinoseb, a herbicide developed in the 1950's. Dinoseb is a contact herbicide that causes injury to peanuts and soybeans; farmers tolerate this injury out of the necessity to control Florida beggarweed. Alternative approaches include MSMA (monosodium methanearsonate) paraquat, toxaphene and triazine herbicides, but these chemicals are not registered for use on these crops for reasons of toxicology and/or crop safety. Other inadequacies of chemical controls include lack of residual control, injury to nontarget organisms, undesirable residues in harvested products and carryover in subsequent crops.

The use of bioherbicides is becoming an increasingly important alternative to chemical herbicides for a variety of reasons, some of which are similar to those experienced in the chemical control of Florida beggarweed, as disclosed above. This importance is accompanied by several patents which have issued for bioherbicides and their use. Some of these patents, by way of illustration, are as follows: U.S. Pat. No. 3,849,104 (control of northern jointvetch with *Colletotrichum gloeosporioides* Penz. aeschynomene); U.S. Pat. No. 3,999,973 (control of prickly sida [teaweed] and other weeds with *Colletotrichum malvarum*); U.S. Pat. No. 4,162,912 (control of milkweed vine with *Araujia mosaic* virus); U.S. Pat. No. 4,263,036 (control of *Hydrilla verticillata* with *Fusarium roseum* Culmorum); U.S. Pat. No. 4,390,360 (control of sicklepod, showy crotalaria, and coffee senna with *Alternaria cassiae*); and U.S. Pat. No. 4,419,120 (control of prickly sida, velvetleaf, and spurred anoda with fungal pathogens.

BRIEF SUMMARY OF THE INVENTION

The subject invention concerns a novel bioherbicide which is effective, when used according to the process disclosed herein, in controlling Florida beggarweed without adversely affecting the growth and yield of the desired field crop. Preferably, the subject invention relates to the use of a composition comprising *Colletotrichum truncatum* (Schw.) Andrus & Moore spores in association with an agricultural carrier wherein said spores are in a concentration of from about $2\times10^4$ spores/ml of carrier to about $2\times10^6$ spores/ml of carrier, to control Florida beggarweed infestation. The concentrated spore formulation can be adapted for distribution over geographical locales or a situs where the spores germinate and infect Florida beggarweed.

DETAILED DESCRIPTION OF THE INVENTION

The fungus *Colletotrichum truncatum* (Schw.) Andrus & Moore is the first fungal pathogen that has been used to control Florida beggarweed. This fungus produces relatively insignificant leaf and stem lesions on mature plants, but causes a devastating disease on seedlings up to the 3–4 leaf stage. The initial symptoms of the disease are a twisting of stems and discoloration of leaf midrib and veins. Leaves eventually become mottled brown-yellow and die.

A subculture of *C. truncatum* (Schw.) Andrus & Moore has been deposited in the permanent collection of the Northern Regional Research Laboratory, U.S. Department of Agriculture, Peoria, Ill., USA, on Feb. 19, 1985. The culture was assigned the accession number NRRL 15933 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

Taxonomic characteristics of *Colletotrichum truncatum* (Schw.) Andrus & Moore are as follows:

Colonies on V-8 and malt extract agars are composed of grayish-brown mycelium, becoming dark due to abundant formation of black sclerotia. The sclerotia are irregular in shape, composed of thick-walled, dark brown cells. Acervulate conidiomata erumpent through wheat stem epidermis contain a dense layer of conidiophores. Conidiophores are branched, consisting of dark brown hyphae bearing hyaline phialides at the apex. Numerous stiff, erect, tapered, dark brown setae are also produced in the conidiomata. Setae are variable in length, up to 235 $\mu$m long, with an average length of 165 $\mu$m. Conidia are hyaline, falcate, with narrowly rounded apices, guttulate, one-celled, but sometimes becoming septate prior to germination. The average size of 50 conidia was 30 $\mu$m long$\times$4 $\mu$m wide (25–35$\times$3.3–4.4 $\mu$m). Appresoria are dark, clavate to irregular in shape, averaging 9.2 $\mu$m long$\times$7 $\mu$m wide (7.7–10.7$\times$5.4–9.2 $\mu$m).

The conidial size is somewhat larger than that recorded by Sutton (Sutton, B. [1980] The Coelomycetes, Fungi imperfecti with pycnidia acervuli and stromata, Commonwealth Mycological Institute, Surrey, England) for this species, but it agrees better with the data from legumes reported by Tiffany and Gilman (Tiffany, L. H. and Gilman, J. C. [1954] Species of Colletotrichum from legumes, *Mycologia*, 46:52–75.

*C. truncatum* can be grown on solid or in liquid media. Solid media that can be used include water agar, potato dextrose agar, V-8 agar and string bean agar (strained extract of macerated string beans solidified in agar). Spores are produced on solid V-8 medium exposed to florescent light. Specifically, solid media can be, for example, (1) water agar, (2) potato dextrose agar (Difco), (3) lima bean agar (Difco), (4) corn meal agar (Difco), (5) potato-carrot agar (Tuite 19), and (6) Desmodium agar (blend 10 gm Desmodium plant parts or plant extracts in 1000 ml water and solidify with 20 gm agar).

For large scale production in fermentation tanks, liquid media is used, for example:

| Formula I - Modified Richard's Solution - V-8* | |
|---|---|
| Sucrose | 50 gm |
| Potassium nitrate | 10 gm |
| Potassium phosphate, monobasic | 5.0 gm |
| Magnesium sulfate.7 H$_2$O | 2.50 gm |
| Ferric chloride | 0.02 gm |
| V-8 juice | 15 ml |
| Distilled water to make | 1000 ml |

*Trademark, The Campbell Soup Company for mixed vegetable juices.

Formula II—Modified Richard's Solution—Distillers Solubles—Same as Formula I but substitute 15 gm Distillers solubles for V-8 juice.

Formula III—Modified Richard's Solution—Brewers yeast—Same as Formula I above but substitute 15 gm brewers yeast for V-8 juice.

Formula IV—Modifed Richard's Solution—Torula Yeast—Same as Formula I above but substitute 16 gm torula yeast for V-8 juice.

Formula V—Oatmeal Solution—2%—20 gm oatmeal blended in 1000 ml distilled water.

Formula VI—Oatmeal Solution—4%+2% sugar—
40 gm oatmeal
20 gm sucrose
1000 ml distilled water Formula VII—Beggarweed Broth—
20 gm beggarweed leaves and petioles
10 gm potassium nitrate
2.5 gm magnesium sulfate 7H$_2$O
10 gm potassium phosphate dibasic
1000 ml distilled water
Adjust final pH to 6.8

The preparation of spores is commenced in preseed liter flasks containing about 300 ml of liquid medium which have been inoculated with spores. The medium is incubated for 1–3 days with agitation at a temperature of about 26° to about 30° C.

The preseed is then transferred aseptically to 20-liter seed tanks with additional sterile medium as described above. The tanks are provided with sterile air and agitation. The cycle is continued at a temperature of about 26° to about 30° C. for 1 to 3 days.

Larger fermentors (250 liter) are aseptically inoculated with the seed tanks (entire contents), described above. Additional sterile medium, as used above, is added and the pH is adjusted to about 6.0. The fermentor is supplied with sterile air and agitation, and is maintained at a temperature of about 26° to about 30° C. for from 1 to 3 days. The fermentor is then harvested by filtering the contents to remove insoluble solids and mycelia growth. The filtered beer is then centrifuged, the supernatant is discarded, and the remaining spore concentrate is resuspended in water and centrifuged again. The supernate is again discarded and the spore concentrate is collected, placed in plastic bags and stored in ice. The concentrate so stored maintains an 80% germination for up to 21 days.

The spore concentrate is mixed with an agriculturally acceptable diluent or carrier for application to the undesired host vegetation or a situs. By the term "situs" is meant those areas infested with the undesired vegetation or potential infestation sites.

The preferred carrier is water, and the spore concentrate is dispersed to make a concentration of from about $2\times10^4$ to $2\times10^6$ spores/ml. The formulation is then sprayed on the undesired vegetation or situs by conventional spraying equipment in an amount of from about 50 to 500 liters per hectare. Applications have been made to Florida beggarweed in the cotyledon to 6-leaf stage at temperatures from 20° to 30° C. Applications are most effective on seedlings with 1–3 leaves to 25° to 30° C.

The fungus is not pathogenic to "Florunner" peanuts or "Centennial" soybeans with spore concentrations up to $2\times10^5$.

Spores of *C. truncatum* (Schw.) Andrus & Moore can be mixed with those of *Alternaria cassiae* to enlarge the scope of control of undesired vegetation. For example, this mixture can be used to control both Florida beggarweed and sicklepod (*Cassia obtusifolia*), the two most troublesome weeds in soybeans and peanuts in the Southeast. Further, spores of *C. truncatum* (Schw.) Andrus & Moore can be mixed with those of *A. cassiae* to control Florida beggarweed adn showy crotalaria or coffee senna. The use of *A. cassiae* to control sicklepod, showy crotalaria and coffee senna is disclosed in U.S. Pat. No. 4,390,360, which is incorporated herein by reference thereto. The culture, means of growing, and application to these weeds disclosed in U.S. Pat. No. 4,390,360 can be used herein. Mixtures of *C. truncatum* and *A. cassiae*, for example, *A. cassiae* NRRL 12533, can be made by methods well known in the art, utilizing the disclosure of U.S. Pat. No. 4,390,360 and that contained herein.

Though spores are the preferred form of the fungi, the fungi also can be used in their vegetative form. For example, fragmented mycelia can be formulated and applied to Florida beggarweed and/or sicklepod, or showy crotalaria, or coffee senna in much the same manner as described above for the spore form.

Following are tabulated results showing the effectiveness of *C. truncatum* in controlling Florida beggarweed:

TABLE I

Effect of Inoculum Level on Anthracnose of Florida Beggarweed

| Thousand spores per ml[1] | Proportion of plants dead in one week[2] % | Visual control rating[3] % | Plant survival after 12 days[4] % |
|---|---|---|---|
| 0 | 0 | 0 | 100 |
| 25 | 49 | 62 | 35 |
| 50 | 57 | 65 | 30 |
| 100 | 57 | 74 | 30 |
| 250 | 60 | 81 | 20 |
| 500 | 74 | 97 | 6 |
| 1000 | 86 | 96 | 7 |

[1]Two-leaf stage plants sprayed to runoff 10-12-84, five replications.
[2]Based on actual counts.
[3]Visual estimate of % diseased tissue.
[4]Proportion of plants with at least one normal leaf.

TABLE II

| Temperature C. | Dead % | Necrotic Tissue % |
|---|---|---|
| 20 | 17.32 | 6.26 |
| 25 | 24.70 | 7.15 |
| 30 | 19.12 | 5.85 |

Data are based on plants grown in three growth chambers at the temperatures indicated. Plants were sprayed to runoff with $5 \times 10^4$ spores per ml, and covered with plastic bags for 48 hr. Ratings were made 7 days after treatment. Data are means of 3 replications.

TABLE III

| Effect of Duration of Moist Period on Disease | | |
|---|---|---|
| Hours | Dead % | Necrotic Tissue % |
| 4 | 0 | 0.275 |
| 8 | 0 | 1.988 |
| 12 | 3.365 | 4.859 |
| 24 | 24.401 | 9.174 |
| 48 | 45.068 | 12.159 |

Data are means of four replications of growth chamber-grown plants treated in the 3-4 leaf stage with $5 \times 10^4$ spores per ml to runoff and covered with plastic bags for the time indicated.

We claim:

1. A composition for agricultural application for controlling Florida beggarweed comprising an isolate of the fungus *Colletotrichum truncatum* (Schw.) Andrus & Moore having the identifying characteristics of culture deposit NRRL 15933, which isolate controls Florida beggarweed without adversely affecting peanuts or soybeans, in association with an inert agricultural carrier.

2. A composition, according to claim 1, wherein said isolate is in the spore form at a spore concentration of from about $2 \times 10^4$ to about $2 \times 10^6$ spores/ml of carrier.

3. A process for controlling Florida beggarweed which comprises applying an effective amount of an isolate of the fungus *Colletotrichum truncatum* (Schw.) Andrus & Moore having the identifying characteristics of culture deposit NRRL 15933, which isolate controls Florida beggarweed without adversely affecting peanuts or soybeans, onto said Florida beggarweed or unto the situs of said Florida beggarweed.

4. A composition for agricultural application for controlling Florida beggarweed and sicklepod or showy crotalaria or coffee senna comprising a mixture of the fungi *Colletotrichum truncatum* (Schw.) Andrus & Moore and *Alternaria cassiae* having the identifying characteristics of culture deposit NRRL 12553 in association with an inert agricultural carrier.

5. A process for controlling Florida beggarweed and sicklepod, or showy crotalaria, or coffee senna which comprises applying an effective amount of a mixture of fungi consisting of an isolate of *Colletotrichum truncatum* (Schw.) Andrus & Moore having the identifying characteristics of culture deposit NRRL 15933, which isolate controls Florida beggarweed without adversely affecting peanuts or soybeans, and *Alternaria cassaie* having the identifying characteristics of culture deposit NRRL 12553 onto said Florida beggarweed and sicklepod, or showy crotalaria, or coffee senna or unto the situs of said Florida beggarweed and sicklepod, or showy crotalaria, or coffee senna.

6. A novel *Colletotrichum truncatum* characterized as having the property of controlling Florida beggarweed without adversely affecting peanuts and soybeans, and, when in its essentially biologically pure form, has the taxonomic characterization of *C. truncatum* (Schw.) Andrus & Moore culture deposit NRRL 15933.

* * * * *

UNITED STATES PATENT AND TRADEMARK OFFICE
CERTIFICATE OF CORRECTION

PATENT NO.   : 4,643,756
DATED        : Feb. 17, 1987
INVENTOR(S)  : Cardina et al.

It is certified that error appears in the above-identified patent and that said Letters Patent are hereby corrected as shown below:

Col. 2, line 21: After "pathogens" insert --)--.
Col. 4, line 56: Delete "adn" and insert --and--.
Col. 6, line 28: After "Moore" insert --having the identifying characteristics of culture deposit NRRL 15933--.

Signed and Sealed this

Twenty-fourth Day of November, 1987

Attest:

DONALD J. QUIGG

*Attesting Officer*   *Commissioner of Patents and Trademarks*